United States Patent [19]

Smith

[11] Patent Number: 4,601,075

[45] Date of Patent: Jul. 22, 1986

[54] EMERGENCY STRETCHER

[76] Inventor: J. Rudy Smith, 1239 Ridge Ave., Philadelphia, Pa. 19123

[21] Appl. No.: 731,298

[22] Filed: May 7, 1985

Related U.S. Application Data

[63] Continuation-in-part of Ser. No. 574,040, Jan. 26, 1984, abandoned.

[51] Int. Cl.[4] .......... A61G 1/00; A61F 5/01

[52] U.S. Cl. .......... 5/82 R; 5/436; 128/134

[58] Field of Search .......... 5/82 R, 434, 436, 424; 128/133, 134, 87 R

[56] References Cited

U.S. PATENT DOCUMENTS 2,489,828 11/1949 Springer .......... 5/82 R
2,788,530 4/1957 Ferguson .......... 5/82 R
3,158,875 12/1964 Fletcher .......... 5/82 R
4,034,748 7/1977 Winner .......... 5/82 R
4,124,908 11/1978 Burns et al. .......... 5/82 R
4,211,218 7/1980 Kendrick .......... 5/82 R
4,297,994 11/1981 Bashaw .......... 128/133
4,506,664 3/1985 Brault .......... 5/82 R

*Primary Examiner*—Alexander Grosz
*Attorney, Agent, or Firm*—Robert K. Youtie

[57] ABSTRACT

A stretcher including an elongate pocket of flexible sheet material adapted to removably receive and retain an elongate stiffener of a width up to that of the pocket, an elongate torso girding part extending transversely across and secured to the pocket at the crossing region spaced laterally between the side edges of the pocket, said torso girding part being rigidified adjacent to the pocket for effecting firm underarm support to the person on the pocket enveloped by the girding part, and straps for securing an enveloped person in position relative to a pocket containing a board of any possible width.

12 Claims, 16 Drawing Figures

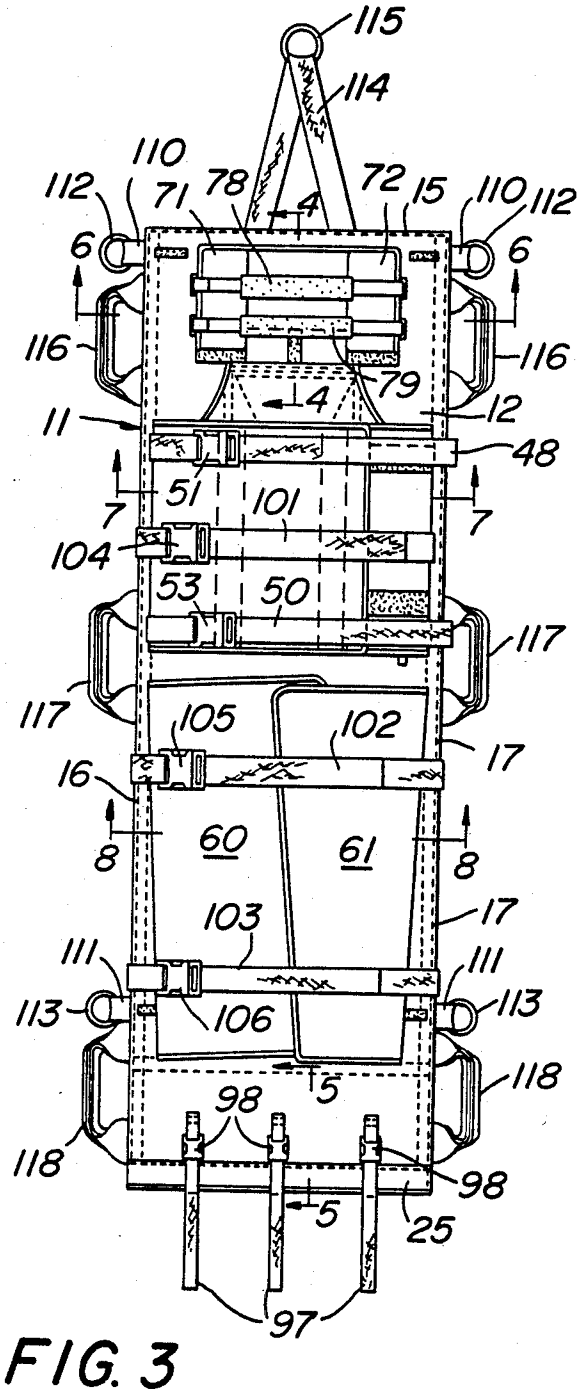
FIG. 3
FIG. 4
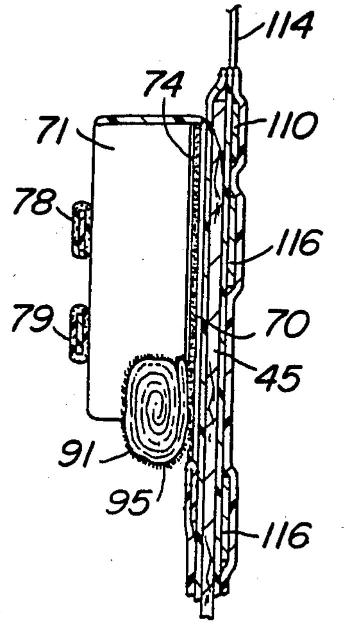
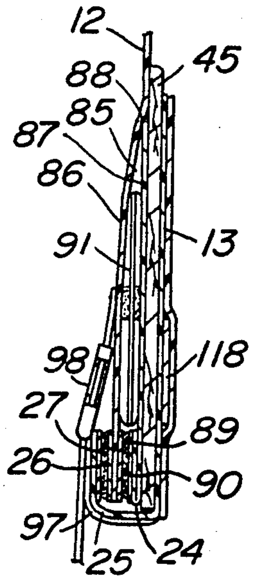
FIG. 5

FIG. 6
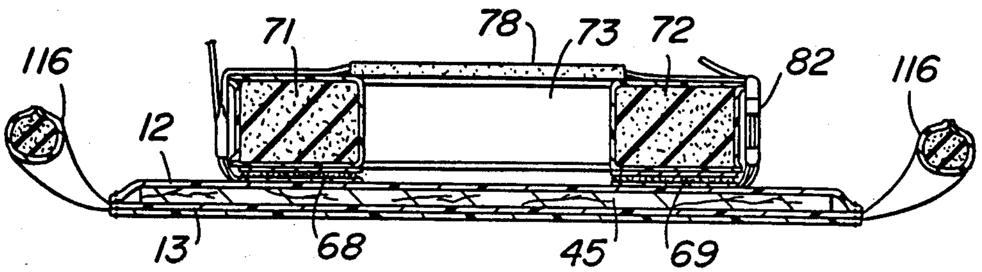
FIG. 7
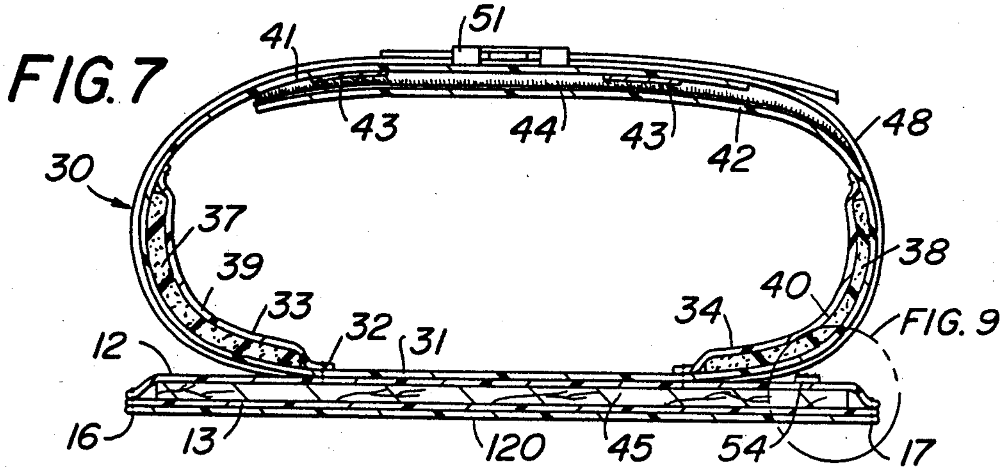
FIG. 9
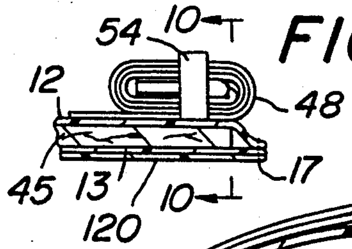
FIG. 10
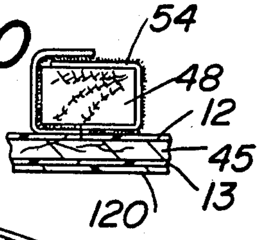
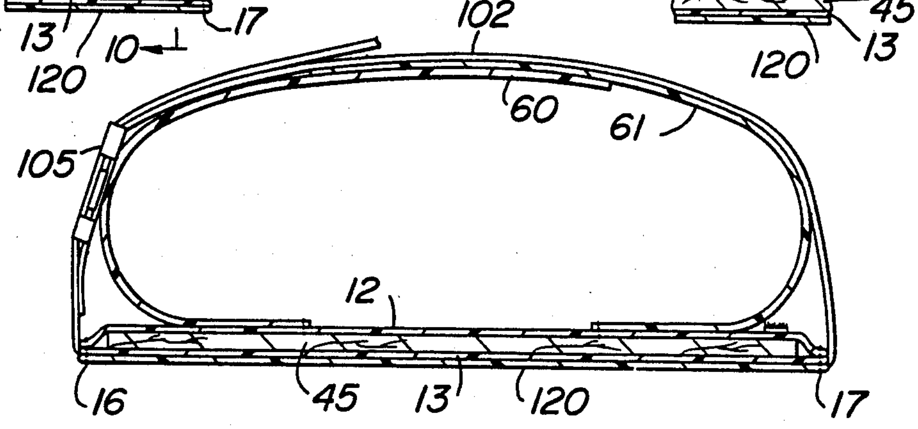
FIG. 8

FIG. 11
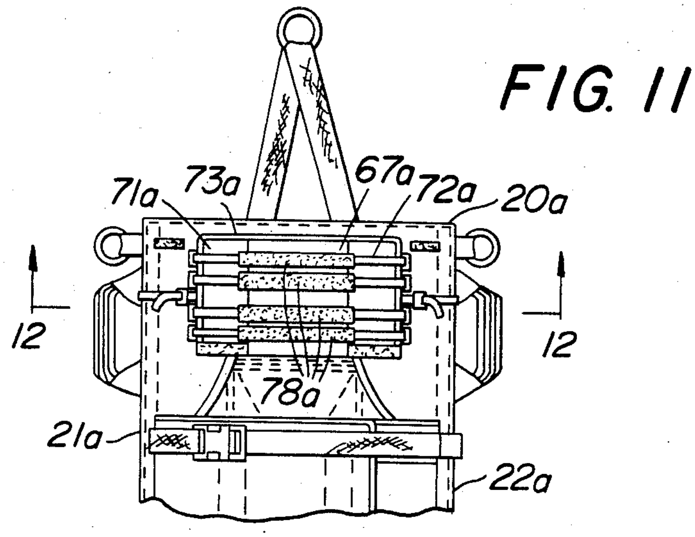
FIG. 12
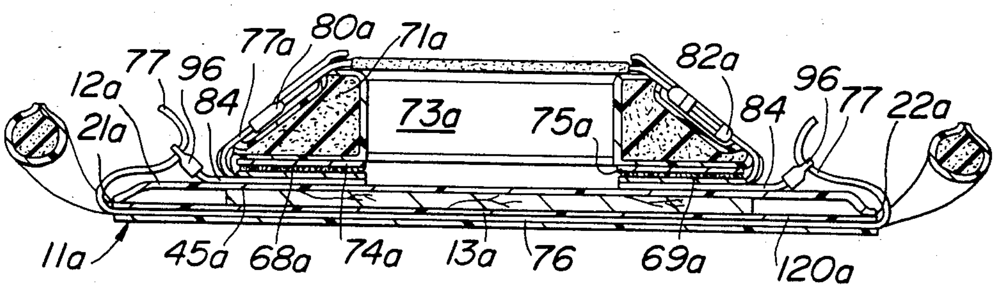
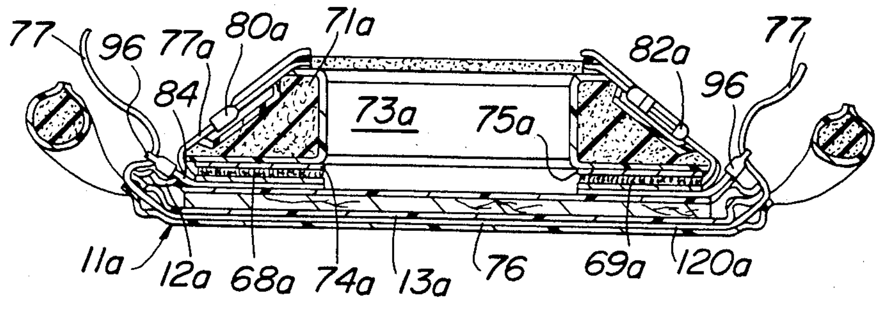
FIG. 13

FIG. 14
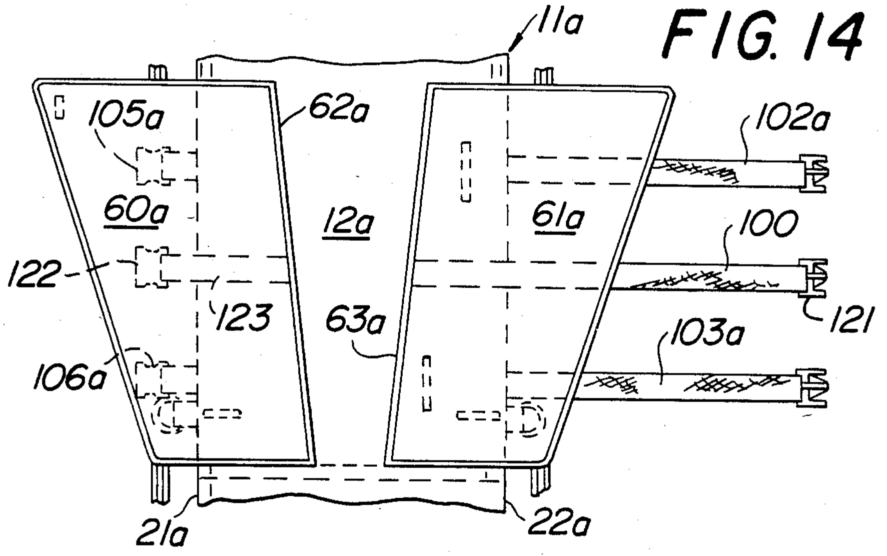
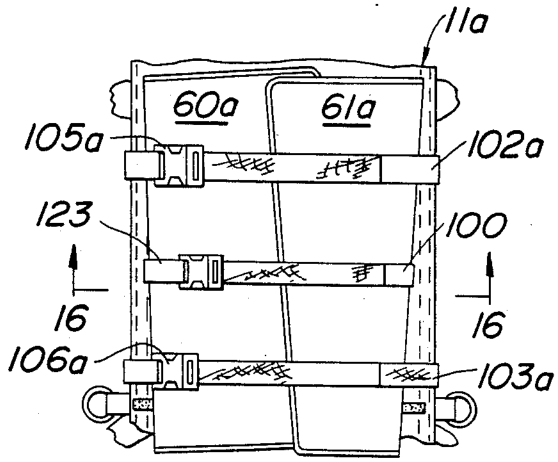
FIG. 15
FIG. 16
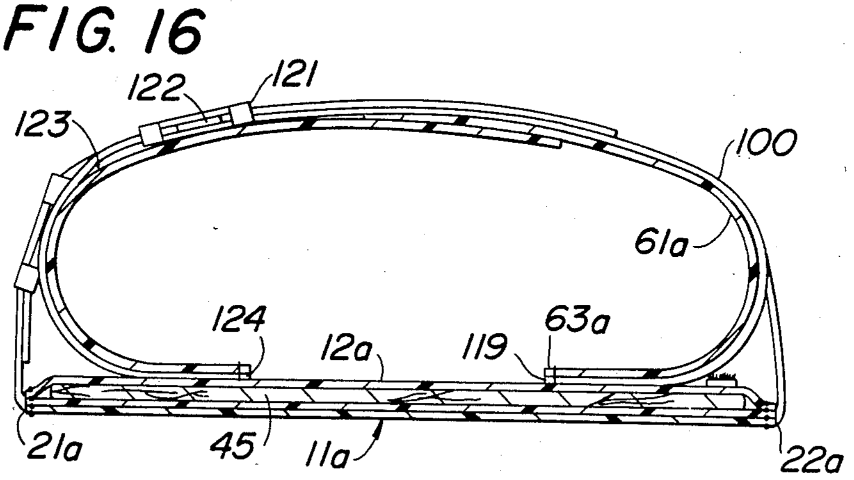

EMERGENCY STRETCHER

CROSS-REFERENCES TO RELATED APPLICATIONS

This application is a Continuation-in-Part of U.S. Patents application Ser. No. 574,040, filed Jan. 26, 1984, now abandoned.

BACKGROUND OF THE INVENTION

While the stretcher art has been highly developed over a long period of time, prior stretchers have suffered certain drawbacks, including tedious and time consuming operating procedures required for use, bulk in handling and storage, and less than desired reliability for use in all situations.

Particularly problematic in the prior art is the provision of a stretcher which is well adapted to meet a wide variety of emergency situations arising. For example, due to the nature of a particular accident there may be required the use of a stiffening board with the stretcher; and circumstances may require that the board be of a particular width; or, the circumstances may prohibit the use of any board, as when the body of a person must be flexed for removal. Also, it may be required that the body of the victim, at any or all locations of the body, must be held fast to the stiffening board, regardless of board width. Prior art devices are incapable of meeting all of the above criteria.

Applicant is aware of the prior art listed below:

| U.S. PAT. NO. | PATENTEE |
|---|---|
| 722,456 | Reeves |
| 2,279,694 | Martinson |
| 2,350,573 | Smith et al. |
| 2,361,328 | Springer |
| 2,489,828 | Springer |
| 2,788,530 | Ferguson |
| 2,899,692 | Finken |
| 3,158,875 | Fletcher |
| 3,343,180 | Lothschuetz |
| 3,566,422 | Klippel |
| 4,034,748 | Winner |
| 4,124,908 | Burns et al. |
| 4,211,218 | Kendrick |
| 4,297,994 | Bashaw |
| 4,301,791 | Franco |
| 4,347,635 | Eisenhauer |

SUMMARY OF THE INVENTION

Accordingly, it is an important object of the present invention to provide a highly improved stretcher which greatly facilitates use, so as to increase speed of rescue operation, effectively secures and immobilizes the person being rescued, and which is adapted to be neatly compacted into a relatively small space for storage and transportation, as in a relatively crowded ambulance, or the like.

It is a further object of the present invention to provide a stretcher having the advantageous characteristics mentioned in the preceding paragraph, wherein a rigidifying spine or backboard may be employed or omitted, as desired; and further wherein rigidity may be achieved with a standard backboard, regular or bi-fold metal backboards, scoop litter, or with any sturdy plank or other material at hand. Further, effective confinement and immobility of the patient is not dependent upon or adversely effected by the size or type of stiffener employed; and alternatively if desired, the stretcher of the instant invention may be employed without any stiffener, as when it is required to flex the person of the patient, or for other reason.

It is a further object of the present invention to provide a stretcher which effectively confines the patient for transport in an emergency with a patient horizontal, vertical, or even upside down, should this be necessary.

It is a further object of the present invention to provide a stretcher of the type described wherein a unique structure in the head rest area assures immobility to the patient, being highly versatile for immobilizing patients of widely varying sizes and shapes.

It is still another object of the present invention to provide a stretcher having the advantageous characteristics mentioned in the preceding paragraphs, which is extremely simple in structure, inherently sturdy in construction for reliable operation throughout a long useful life, and which otherwise fully accomplishes its intended objects.

Other objects of the present invention will become apparent upon reading the following specification and referring to the accompanying drawings, which form a material part of this disclosure.

The invention accordingly consists in the features of construction, combinations of elements, and arrangements of parts, which will be exemplified in the construction hereinafter described, and of which the scope will be indicated by the appended claims.

BRIEF DESCRIPTION OF THE DRAWINGS

FIG. 3 is a top plan view showing the stretcher in an operative condition, but absent a patient's body to facilitate understanding.

FIG. 4 is a partial longitudinal sectional view taken generally along the line 4—4 of FIG. 3.

FIG. 5 is a partial longitudinal sectional view taken generally along the line 5—5 of FIG. 3.

FIG. 6 is a transverse sectional view taken generally along the line 6—6 of FIG. 3.

FIG. 7 is a transverse sectional view taken generally along the line 7—7 of FIG. 3.

FIG. 8 is a transverse sectional view taken generally along the line 8—8 of FIG. 3.

FIG. 9 is a partial sectional view in the correspondingly designated area of FIG. 7, but with the strap in its nonuse condition.

FIG. 10 is a sectional elevational view taken generally along the line 10—10 of FIG. 9.

FIG. 11 is a partial top plan view similar to FIG. 3, but showing a slightly modified embodiment of the instant invention.

FIG. 12 a transverse sectional view taken generally along the line 12—12 of FIG. 11, but showing a stiffener board of less than maximum width.

FIG. 13 is a sectional view similar to FIG. 12, but illustrating constriction of the board receiving pocket closely about the board.

FIG. 14 is a partial top plan view similar to FIG. 1, but showing a slightly modified embodiment including an additional strap extending from laterally intermediate regions of the pocket for wrapping about a person's limbs.

FIG. 15 is a plan view similar to FIG. 3, but showing the embodiment of FIG. 14.

FIG. 16 is a transverse sectional view taken generally along the line 16—16 of FIG. 15.

DESCRIPTION OF THE PREFERRED EMBODIMENT

Figure 1:
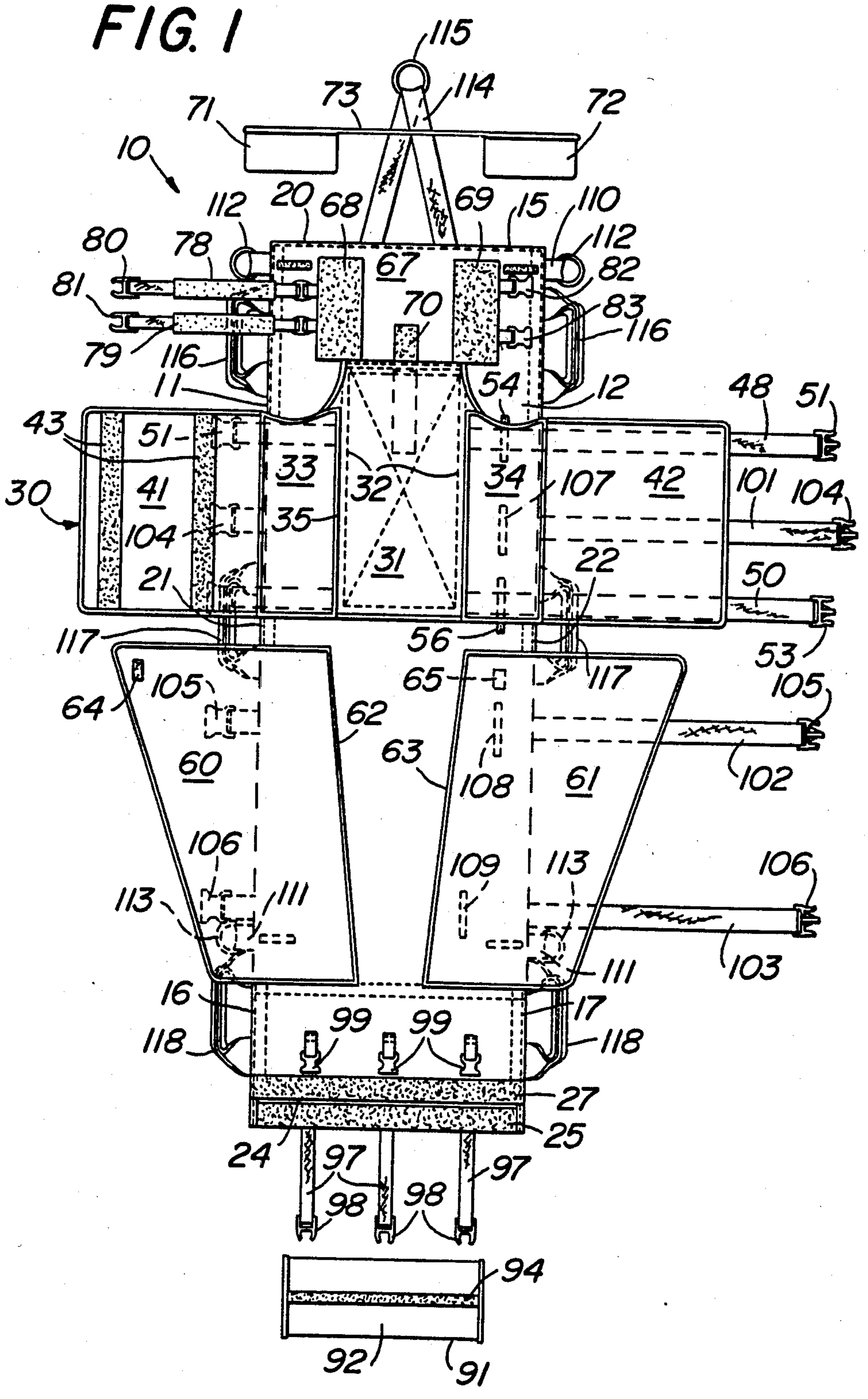
FIG. 1 is a top plan view showing a stretcher of the present invention in an open condition preparatory for use.
Figure 2:
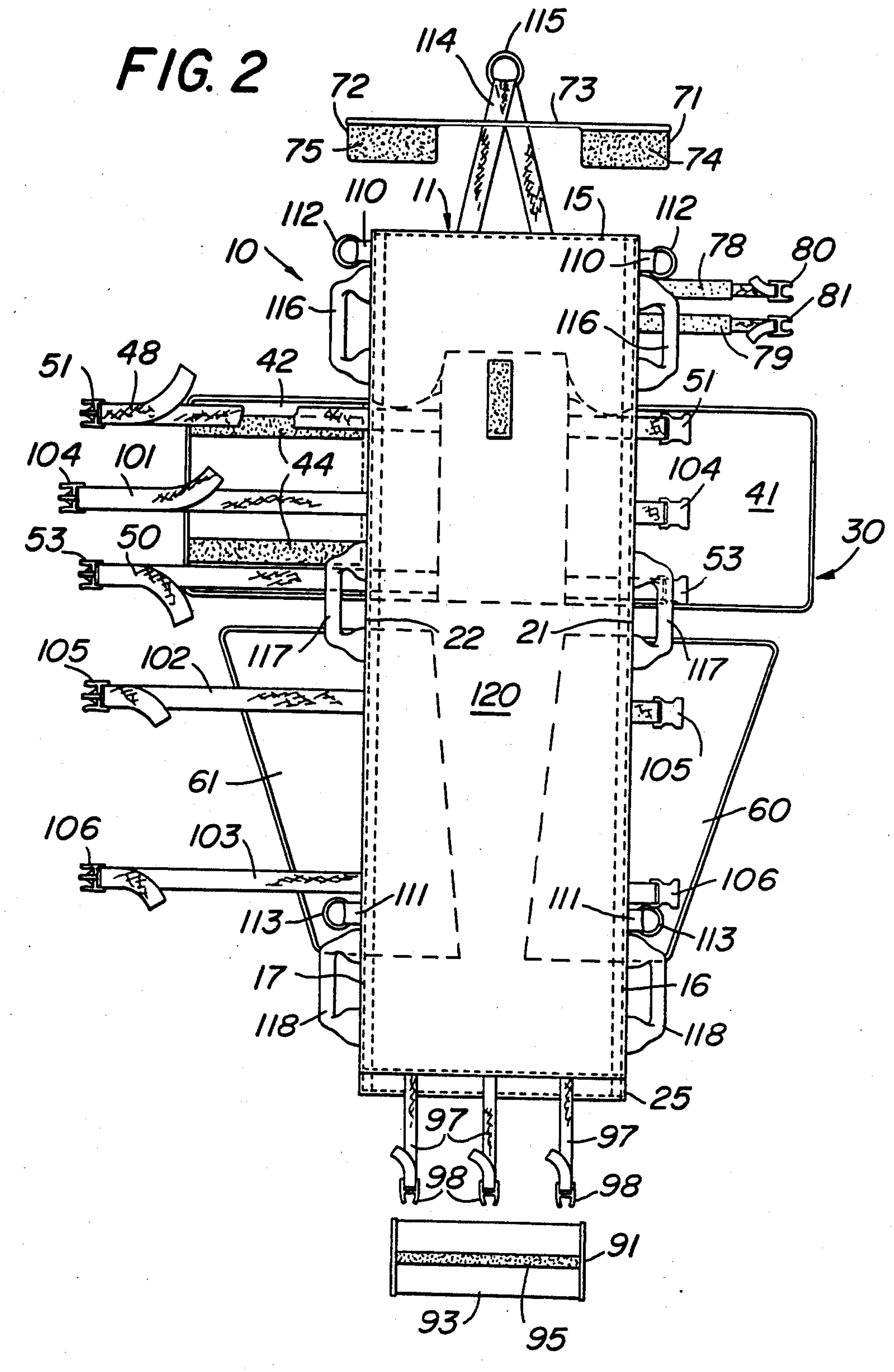
FIG. 2 is a bottom plan view showing the stretcher of FIG. 1.

Referring now more particularly to the drawings, and specifically to FIGS. 1-3 thereof, the stretcher is there generally designated 10 and includes an elongate generally flat pocket or sleeve 11. The pocket or sleeve 11 may be fabricated of suitable flexible sheet material, including a pair of generally rectangular, substantially congruent, overlying inner and outer sheets 12 and 13, which sheets are seen as upper and lower in FIGS. 6-8. The upper sheet 12 is secured along one end to the adjacent end of the lower sheet 13, as by securement means or stitching 15 extending laterally between opposite side edges of the sheets 12 and 13. Further, the sheets 12 and 13 are secured together along longitudinal side edges by suitable securing means or stitching, as at 16 and 17. Thus, the pocket or sleeve 11 has one end closed, as by stitching or closure means 15 at one sleeve end 20, and has its opposite longitudinal or side edges closed, as at 21 and 22, each closed side extending the entire length of the sleeve. The opposite end of the sleeve 11, remote from the closed end 20, is open, as at 24, and provided on the end of the lower or outer sheet 13 with an extension or flap 25. The extension or flap 25 is laterally coextensive with the pocket 11; and, there are provided on the flap 25 and adjacent end portion of sheet 12 a pair of complementary, detachably connectible, laterally extending strips or pieces of fastener fabric 26 and 27. By this construction, the flap 25 is foldable over the pocket end opening 24 to substantially completely close the latter, and the fabric fastener elements 26 and 27 are engaged to effectively retain the flap in its folded, pocket end closing relation as shown in FIG. 5.

At a longitudinally intermediate location on the upper or inner sheet 12 of the pocket 11, spaced between the closed and open pocket ends 20 and 24, there is provided a torso girding part, generally designated 30 and essentially fabricated from a single piece of flexible sheet material extending transversely across and beyond opposite side edges 21 and 22 of the pocket 11. The torso girding part 30 includes a medial, generally rectangular region 31 suitably secured by stitching 32 or other suitable securing means, to the upper surface of upper sheet 12. More particularly, the secured medial region 31 of torso girding part 30 is spaced laterally between the side edges 21 and 22 of the pocket 11, the securing means 32 being spaced inwardly from the side edges.

Extending laterally outwardly from opposite sides of medial region 31, the torso girding part includes a pair of intermediate portions or panels 33 and 34, which are swingably or hingedly connected to respective side edges of the medial region 31, so as to be swingable upwardly away from the pocket 11. More specifically, the intermediate panels 33 and 34 are each swingably or hingedly connected, as by a respective flexible connection 35 and 36, to the adjacent side edge of medial panel 31; and, the panels 33 and 34 are advantageously stiffened or rigidified, as by securement thereto of stiffener means or padding, as at 37 and 38 best seen in FIG. 7. The stiffener elements or padding 37 and 38 may be secured to the torso girding part 30 by respective covering sheets 39 and 40.

From the outer, swingable region of each intermediate stiffened part 33 and 34, there extends a flexible covering flap or sheet, as at 41 and 42. As best seen in FIG. 7, the torso girding part 30 may include, as a single integral sheet, the medial portion 31, the intermediate portions 33 and 34 extending from opposite sides of the medial portion, and the outer end extensions or flaps 41 and 42 extending from respective intermediate portions 33 and 34.

In practice, a rescuee may rest with his torso on the medial region 31 and the stiffened intermediate regions 33 and 34 swung upwardly to afford effective underarm support to the rescuee.

The extension flaps or terminal portions 41 and 42 of the torso girding part 30 are swung over the rescuee, in overlying relation with each other, and provided with detachable securing means, preferably in the form of fastener fabric strips, as at 43, extending longitudinally on the upper surface of extension 41, and 44 extending laterally on the inner surface of extension 42. The fastener fabric strips are suitably secured to the extensions, as by stitching or otherwise, the outwardly facing fastener fabric strips 43 extending longitudinally of the pocket or sleeve 11, and the inwardly or downwardly facing fastener fabric strips 44 extending laterally or transversely of the pocket or sleeve. In use, the extension 42 is necessarily swung first to overly the rescuee, and the extension 41 subsequently swung to overly the rescuee and the extension 42. This places the fastener fabric strips in transversely extending, facing engagement and secured together to maintain the extensions in their overlying relationship.

Additional fastener means are provided for securing the torso girding part 30 in its torso girding relation, such as a plurality of belts or straps 48 and 50, which are suitably secured to and between the medial torso girding portion 31 and the adjacent portion of pocket sheet 12. That is, by suitable stitching, as at 32, intermediate portions of the several belts or straps 48, 50 are secured between the medial torso girding portion 31 and the nether region of pocket sheet 12; and, the belts or straps extend oppositely outwardly beyond the medial region free of the pocket for extension about the exterior of the wrapped torso girding part 30 with its extensions 41 and 42 overlying each other. Oppositely extending free ends of the straps 48 and 50 are provided with detachably connectible fastening elements or buckles, as at 51 and 53.

In addition, binding strips may be provided or secured on the upper surface of pocket wall 12, as at 54 and 56, for releasable binding about the straps 48 and 50 when the latter are in a coiled, nonuse condition. The binding straps or strips 54 and 56 may also be of fastener fabric, if desired.

Also secured to the upper or outer face of pocket wall 12, spaced between the torso girding part 30 and the open pocket end 24, are a pair of flexible limb girding sheets or flaps 60 and 61. The limb girding sheets or flaps are disposed in side by side spaced relation, each having its inner edge margin suitably secured, as by stitching, to the upper or outer wall 12 of pocket 11. Thus, the inner margin 62 of limb girding flap 60 is secured to the exterior of pocket wall 12 at a location along and spaced inward from the pocket side edge 21, while the inner edge margin 63 of the limb girding flap 61 is suitably stitched or otherwise secured to the outer surface of pocket wall 12 along and spaced inward from the pocket side edge 22. The flaps 60 and 61 are thus secured to the pocket only along their inner edges 62 and 63, the remainders thereof being free to swing about and overlie the limbs of a rescuee on the wall 12 of pocket 11. The limb girding flaps 60 and 61 may taper in the direction toward the open pocket end 24, to accomodate to the decreasing proportions of a person and minimize bulk of the device. In the storage condition, the flap 61 may be swung inward to overlie the laterally medial region of pocket wall 12, and flap 60 swung inwardly to overlie the flap 61. A pair of mating patches of fastener fabric may be secured to the outer flap 60, as at 64, and to the wall 12, as at 65, to secure the flaps in the nonuse condition.

Intermediate the torso girding part 30 and the closed end 20 of the pocket 11, laterally medially between the pocket side edges 21 and 22, there is a head rest area 67. On opposite sides of the head rest area 67, spaced laterally inwardly from pocket side edges 21 and 22 are pieces 68 and 69 of fastener fabric suitably secured, as by stitching or otherwise, to the outer surface of pocket wall 12. The fastener fabric pieces 68 and 69 are generally elongate, and extend in parallelism with each other longitudinally of the pocket 11. An additional longitudinally extending strip of fastener fabric 70 is secured to the pocket wall 12, spaced laterally between the pieces 68 and 69, and adjacent to the medial region 31 of the torso girding part 30.

A pair of elongate cushions or cushioned bodies 71 and 72 are connected together by a flexible tie member or strip 73 extending between adjacent ends of the cushions. Carried by the cushions 71 and 72, on the undersides thereof, are elements of fastener fabric, as at 74 and 75 for respective mating engagement with fabric fastener pieces 68 and 69. Thus, the cushions 71 and 72 may seat on and be detachably secured to the fabric fastener piece 68 and 69, with the flexible tie member 73 extending between the ends of the cushions adjacent to the closed end 20 of the pocket 11. This condition is shown in FIG. 3.

In addition, a pair of straps 78 and 79 may be secured to the pocket wall 12, say beneath the fastener fabric piece 68 and extending laterally outwardly therefrom to terminate in connector elements 80 and 81. Secured to the wall 12 beneath the fastener fabric piece 69 and extending laterally therefrom may be additional strap connector elements 82 and 83 for detachable connection to respective strap connector elements 80 and 81. Thus, the strap means 78 and 79 is adapted to extend releasably over the cushion bodies 71 and 72 and across the head rest area 67, as seen in FIG. 3, for holding the cushions and a person's head in position on the pocket 11.

The pocket or sleeve 11 is provided adjacent to its open lower end 24 with a subpocket 85, see FIG. 5, defined between the lower end region 86 of wall 12 and a generally rectangular pocket sheet 87 interposed between the walls 12 and 13 and secured to the wall 12, as by transverse stitching 88 and longitudinal stitching 16 and 17 along the respective side edges 21 and 22 of the pocket 11. Thus, the subpocket 85 is generally rectangular, laterally coextensive with the pocket or sleeve 11, and opens longitudinally outwardly of the sleeve 11 through the open sleeve end 24. Separable fastener means may be provided along the opening of the subpocket 85, such as separable fastener fabric strips 89 and 90. Removably positioned in the interior of closed pocket 85, as seen in FIG. 5, is a generally flat neck support or cushion 91. The cushion 91 is seen in FIGS. 1 and 2 apart from the sleeve 11 exteriorly of the subpocket 85. The neck cushion 91 may be generally rectangular and essentially flat for conforming engagement and storage in the subpocket 85, including generally rectangular opposite faces or sides 92 and 93, as seen in FIGS. 1 and 2, respectively. The longitudinal dimension or length of the cushion 91 extends laterally or transversely of the pocket or sleeve 11, as does the longitudinal dimension or length of the subpocket 81 to conformably accomodate the neck cushion. Secured on one face or side 92 of the neck cushion 91, extending longitudinally therealong and spaced laterally medially between the side edges of the neck cushion is a strip of fastener fabric 94. On the other side or face 93 of the neck cushion 91 there is secured an elongate strip of complementary fastener fabric 95, also extending longitudinally coterminous with the cushion, laterally spaced medially between the longitudinal side edges thereof. Upon longitudinal rolling or coiling of the cushion 91 about lateral axes, it will be appreciated that one of the fastener fabric strips 94 or 95 will be rolled into holding engagement with the other fastener fabric strip 95 or 94, respectively. By this arrangement, the neck cushion 91 will be self holding in any longitudinal rolled or coiled condition, such as tight, loose, etc. The neck cushion 91 is illustrated rolled in FIG. 4, with one of the fastener fabric strips 94, 95 exteriorly of and exposed peripherally about the coil. It will there be observed that the coil 91 is seated on the fastener fabric piece 70 secured in the head rest region 67 of the sheet 12. Thus, the coiled neck rest cushion is securely, but detachably held in position beneath an occupant's neck.

Of course, for storage the neck support cushion 91 may be removed from the head rest area 67 and uncoiled for reinsertion in the subpocket 85.

A plurality of securement straps 97 may be secured to the wall 13 of pocket 11 and extend longitudinally outwardly beyond the open end 24 and closure flap 25. Fastener elements 98 are secured to the free ends of straps 97, and complementary fastener elements 99 are secured to the sheet 12 just inward of the open end 24. Thus, the complementary fastener elements 99 are secured to the sheet 12 just inward of the end 24. The complementary fastener elements 98 and 99 are detachably connectible together to secure the flap 25 in its closed condition against substantial forces. Thus, a rigid board 45 substantially congruent to the pocket 11 may be inserted into the interior of the pocket through the open end 24 to substantially fully occupy the pocket, and may be secured therein both by closing of the flap 25 with adherence of the fabric fastener strips 26 and 27, and by securement of the detachable connectors 98 and 99 with the straps 97 adjusted tightly. If it is not desired to carry a full size board for use in the pocket 11, any smaller size board may be inserted therein to achieve the spine immobilizing effects. In addition, the pocket 11 is adapted to effectively contain a standard backboard, a regular or bi-fold metal backboard, or a conventional scoop litter.

In addition, there are provided extending laterally entirely across the pocket wall 13, exteriorly of the pocket a plurality of girding straps or strips 101, 102 and 103, at longitudinally spaced locations along the pocket 11. Specifically, the strap 101 may extend transversely in the region of torso girding part 30, and the straps 102 and 103 extend transversely in the region of the limb girding flaps 60 and 61. The strap 101 may have detachable connectors 104 at its opposite ends, while the strap 102 has detachable connectors 105 at its opposite ends, and the strap 103 has detachable connectors 106 at its opposite ends. The straps 101, 102 and 103, with their ends connected, encompass both the pocket 11 and the torso and limb girding parts, so as to effectively secure the person of the occupant to a stiffener in the pocket 11.

Binding straps 107, 108 and 109, say of fastener fabric material may be secured to the pocket wall 12, exteriorly thereof, for releasably binding the straps 101, 102 and 103, respectively, when the latter are in a coiled, storage condition.

A pair of laterally extending lifting straps 110 and 111 may extend across and be secured to the outer side of pocket wall 13, adjacent to opposite ends of the pocket 11, and may be provided with lifting eyes 112 and 113, respectively. An end lifting strap 114 may be secured to the outer side of pocket wall 13, extending beyond the pocket end 20, and there provided with a lifting eye or ring 115.

There may also be provided, along each side edge 21 and 22 of the pocket 11 a plurality of hand holds, such as a pair of opposite hand holds 116 extending from opposite sides of the pocket 11 adjacent to the pocket end 20, a pair of opposed hand holds 117 spaced medially between opposite pocket ends, and a pair of opposed hand holds 118 adjacent to the open pocket end 24. The hand holds may be advantageously fabricated of sturdy webbing, and extend entirely across and beyond opposite side edges of the pocket wall 13, being stitched or otherwise suitably secured thereto.

In addition to the pocket sheets 12 and 13, there is another, also substantially congruent flexible covering sheet 120, secured about its peripheral margins to the pocket sheet 13 exteriorly thereof. The covering sheet thus protectively overlies and conceals the several straps 101, 102 and 103, 110, 111 and 114, and the webbing of hand holds 116, 117 and 118. The back of the stretcher, opposite to the surface carrying a rescuee, is thus substantially completely smooth to effectively prevent unintended hang-ups, or the like.

Referring now to the slightly modified embodiment of FIGS. 11, 12 and 13, there is shown a head rest area 67a adjacent to the closed pocket end 20a and spaced between the pocket side edges 21a and 22a. On opposite sides of the head rest area 67a, spaced laterally inwardly from pocket side edges 21a and 22a are pieces 68a and 69a of fastener fabric suitably secured, as by stitching or otherwise, to the outer surface of pocket wall 12a. The fastener fabric pieces 68a and 69a are generally elongate, and extend in parallelism with each other longitudinally of the pocket 11.

A pair of elongate cushions or cushioned bodies 71a and 72a are connected by a flexible tie member or strip 73a extending between adjacent ends of the cushions. Carried by the cushions 71a and 72a, on the undersides thereof, are elements of fastener fabric, as at 74a and 75a for respective mating engagement with fabric fastener pieces 68a and 69a. Thus, the cushions 71 and 72 may seat on and be detachably secured to the fabric fastener pieces 68a and 69a, with the flexible tie member 73a extending between the ends of the cushions adjacent to the closed end 20 of the pocket 11.

As best seen in FIGS. 12 and 13, in this embodiment the cushions 71a and 72a are of generally triangular or wedge shape in transverse cross section, being thicker or heavier on their inner sides facing toward each other, and tapering toward their outer edges away from each other.

In the embodiment of FIGS. 11–13, there are preferably four straps 78a, corresponding to the two straps of the first described embodiment, each of which may be secured to the pocket wall 12a, say beneath the fastener fabric piece 68a and extend laterally outwardly therefrom to terminate in a connector element 80a. Secured to the wall 12a beneath the fastener fabric piece 69a and extending laterally therefrom may be an additional strap connector element 82a for detachable connection to strap connector 80a. The straps 78a are thus adapted to extend releasably over the cushion bodies 71a and 72a for holding the cushions and a person's head in position on the pocket 11.

An additional elongate flexible draw element or strap 76 may extend transversely across and outwardly of the lower, outer pocket wall or sheet 13a, as between the latter and lower covering sheet 120a and extending laterally outwardly therebeyond as by strap end portions 77. The draw elements or straps 77 may be unsecured to the pocket 11a, or may be tacked or secured, say at one location to the pocket so as to permit gathering of the pocket along the draw element.

Secured to the upper side of the pocket 11a, spaced inwardly from the pocket side edges 21a and 22a, as by a pair of straps 84, may be a respective pair of self tightening buckles 96. Thus, the buckles 96 are each aligned with a respective end portion 77 of draw element 76, and the buckles are located laterally inwardly from respective pocket sides or edges 21a and 22a, so that the side edge portions of the pocket, may, under certain circumstance, be gathered up by tightly drawing the strap end portions 77.

This is best seen in FIG. 13, wherein a board 45a is received in the pocket 11a, which board is of less lateral dimension or width than the interior lateral dimension or width of the pocket 11a, as best seen in FIG. 12. Such a board may sometimes be used, either for convenience or necessity, and in such circumstances it may be desired to reduce the effective width of the pocket 11a to constrict the latter closely about the board. This is done by drawing up of the strap end portions 77, to the condition shown in FIG. 13, which condition is held by the buckles 96, until deliberately released.

It will be appreciated that, when the pocket 11a is constricted closely about the received board 45a, the patient may be held closely and firmly to the board and back and forth movement of the patient's body relative to the board is effectively prevented. As illustrated, the draw element of FIGS. 11–13 is in the head region of the pocket 11, so that the patient's head is held against relative movement with respect to the board. Of course, the draw element may, alternatively or additionally, be located at other regions of the pocket, say the torso region or the limb region.

Referring now more particularly to the embodiment of FIGS. 14–16, a pair of flexible limb girding sheets or flaps 60a and 61a are each secured, as along its inner edge margin, as at 62a and 63a, respectively, to the upper or outer wall 12a of the pocket 11a, at locations spaced inwardly from adjacent side edges 21a and 22a of the pocket.

The flaps 60a and 61a may be substantially identical to the flaps 60 and 61 of the first described embodiment; and, there may be girding straps 102a and 103a cooperable with detachable connectors 105a and 106a in the same manner as straps 102 and 103, and connectors 105 and 106.

In addition, the embodiment FIGS. 14–16 includes a girding strap 100 which may have its inner end secured to pocket 11*a* on the upper side thereof spaced inwardly from the pocket edges. For example, see FIG. 16, where the inner end 119 of strap 100 may be secured beneath the inner edge 63*a* of the flap 61*a*, at a location adjacent to and spaced inwardly from the pocket side edge 22*a*. The free end of strap 100 may include a detachable buckle element 121; and, a complementary detachable buckle element 122 which may be carried by a strap portion 123 having its inner end 124 secured to the upper side 12*a* of the pocket 11*a* at a location adjacent to and spaced inward from the pocket side edge 21*a*. The strap 100 and strap portion 123 may be a single integral strap, if desired, or complementary parts of cooperative strap means for extension about the limbs of a person occupying the stretcher. In such case it will be appreciated that the limbs are effectively restrained relative to the pocket and a received board, whether the board is of maximum width or less than maximum width.

The operation is believed obvious from the foregoing description. It may also be appreciated that in the absence of a stiffening board, such as the board 45 in the pocket 11, the entire assembly is fabricated of flexible material, and may be conveniently folded to a compact size occupying a minimum of space.

From the foregoing, it is seen that the device of the present invention provides an emergency stretcher which is extremely fast and easy to use, secure and safe even under difficult operating conditions, and which otherwise fully accomplishes its intended objects.

Although the present invention has been described in some detail by way of illustration and example for purposes of clarity of understanding, it is understood that certain changes and modifications may be made within the spirit of the invention.

What is claimed is:

1. A stretcher comprising an elongate generally rectangular pocket of flexible sheet material having one end closed and the other end open substantially between opposite side edges of said pocket for removably receiving an elongate stiffener of any desired width approximately up to that of said pocket, an openable end closure at said other end of said pocket for removably retaining a stiffener in said pocket, an elongate flexible torso girding part extending transversely across a longitudinally medial region of said pocket, securing means securing said girding part at the crossing region only to a laterally medial portion of said pocket spaced inwardly from the side edges of said pocket with said girding part free from said pocket adjacent to the pocket edges for wrapping closely about the torso of a person on the exterior of said pocket substantially independently of a stiffener, a pair of rigidifying parts carried by and rigidifying said girding part respectively extending outwardly from opposite sides of said securing means for furnishing underarm support to a person on said pocket, first elongate flexible strap means extending transversely across a longitudinally medial region of said pocket and secured to opposite pocket edges for wrapping with said pocket and girding part closely about the torso of a person on said pocket when there is no stiffener or a relatively narrow stiffener in said pocket, said first strap means combining with said girding part to hold a stiffener of less than maximum width firmly toward the wrapped torso, and second elongate flexible strap means extending transversely across a longitudinally medial region of said pocket and secured to said pocket laterally medially of said pocket spaced inwardly from the side edges of said pocket with said strap means free from said pocket adjacent to the pocket edges for wrapping with said girding part closely about the torso of a person substantially independently of a stiffener in said pocket, said second strap means holding a wrapped person laterally medially of said pocket when a stiffener of up to maximum width is located in said pocket.

2. A stretcher according to claim 1, said second strap means extending continuously between pocket and torso girding part and terminating at free outer ends, and detachable connectors on said free outer ends.

3. A stretcher according to claim 1, in combination with a pair of flexible limb girding flaps offset longitudinally of said pocket from said torso girding part and extending from laterally intermediate regions of said pocket oppositely outwardly beyond said pocket for wrapping about the limbs of the person, and a pair of limb holding straps secured to and extending oppositely laterally outwardly from respective side edges of said pocket for wrapping about said limb girding flaps.

4. A stretcher according to claim 3, said limb holding straps extending continuously between opposite side edges of said pocket and terminating in connectable free ends.

5. A stretcher according to claim 1, said end closure comprising an end flap extending from one side of said pocket and swingable onto the other side of said pocket, the end flap fastener means detachably securing said end flap to said other pocket side.

6. A stretcher according to claim 1, said pocket having a head rest area adjacent to the closed pocket end, cushioned bodies on opposite sides of said head rest area for confining a person's head to said area, detachable connection means securing said bodies to said pocket in said head confining position, and strap means releasably extending over said bodies and across said head rest area for holding said bodies and a person's head in position on said pocket.

7. A stretcher according to claim 6, said detachable connection means comprising mating elements of fastener fabric secured to said bodies and pocket.

8. A stretcher according to claim 6, in combination with flexible draw means carried by said pocket in said head rest area for constricting said pocket area closely about a board of less than maximum width in said pocket, for holding a person's head against movement relative to a board in said pocket.

9. A stretcher according to claim 8, said draw means comprising flexible elongate elements extending about said pocket for gathering the latter closely about a received board, and buckle means for releasably securing said elongate elements in drawn condition.

10. A stretcher according to claim 6, said cushion bodies being elongate and disposed in parallel spaced relation with each other longitudinally of said pocket, and a flexible tie member extending between said bodies at one pair of adjacent body ends longitudinally outwardly of said pocket, for constraining said bodies against separation.

11. A stretcher according to claim 1, in combination with mating strips of fastener fabric on opposite end portions of said girding part for movement into and out of securing engagement with each other, said mating strips on opposite end portions of said girding part extending transversely of each other for mating engagement throughout a range of positions of said opposite end portions.

12. A stretcher according to claim 1, in combination with flexible elongate elements extending about said pocket for gathering the latter closely about a received board of less than maximum width in said pocket, and buckle means for releasably securing said elongate elements in drawn condition.

* * * * *